(12) United States Patent
Nousiainen

(10) Patent No.: US 6,545,189 B1
(45) Date of Patent: *Apr. 8, 2003

(54) PROCESS FOR THE PREPARATION OF NEOPENTYL GLYCOL

(75) Inventor: Hannu Nousiainen, Porvoo (FI)

(73) Assignee: Neste Chemicals Oy, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,709

(22) PCT Filed: Dec. 30, 1998

(86) PCT No.: PCT/FI98/01031

§ 371 (c)(1),
(2), (4) Date: Aug. 22, 2000

(87) PCT Pub. No.: WO99/35112

PCT Pub. Date: Jul. 15, 1999

(30) Foreign Application Priority Data

Dec. 30, 1997 (FI) ................................................... 974638

(51) Int. Cl.⁷ .......................... C07C 27/04; C07C 29/14; C07C 31/18
(52) U.S. Cl. ....................................................... 568/862
(58) Field of Search ......................................... 568/862

(56) References Cited

U.S. PATENT DOCUMENTS

| | | | |
|---|---|---|---|
| 2,895,996 A | | 7/1959 | Wright et al. |
| 3,920,760 A | | 11/1975 | Heinz |
| 4,181,810 A | * | 1/1980 | Immel et al. ................ 568/807 |
| 4,851,592 A | | 7/1989 | Morris |
| 4,918,247 A | | 4/1990 | Breitkopf et al. |
| 5,146,012 A | | 9/1992 | Salek et al. |
| 5,395,989 A | * | 3/1995 | Yoneoka et al. ............. 568/862 |
| 6,255,541 B1 | * | 7/2001 | Paatero et al. .............. 568/862 |

FOREIGN PATENT DOCUMENTS

| | | | |
|---|---|---|---|
| DE | 1014089 | | 8/1957 |
| JP | 2000026356 A | * | 1/2000 |
| WO | WO 97/35825 | | 10/1997 |

* cited by examiner

Primary Examiner—Johann Richter
Assistant Examiner—Elvis O. Price
(74) Attorney, Agent, or Firm—Birch, Stewart, Kolasch & Birch, LLP

(57) ABSTRACT

The invention relates to a process for the preparation of neopentyl glycol by hydrogenation of hydroxypivaldehyde (HPA) in the presence of hydrogen and a hydrogenation catalyst at an elevated temperature. According to the invention, hydroxypivaldehyde is hydrogenated in the presence of a nickel-containing catalyst and at a temperature below 100° C. in a liquid phase containing a solvent an amount of 1–70% by weight and water in an amount of 0–15% by weight. Aliphatic alcohol or ether or a mixture thereof is used as solvent.

8 Claims, No Drawings

PROCESS FOR THE PREPARATION OF NEOPENTYL GLYCOL

This application is the national phase under 35 U.S.C. § 371 of PCT International Application No. PCT/FI98/01031 which has an International filing date of Dec. 30, 1998, which designated the United States of America.

The invention relates to a process for the preparation of neopentyl glycol. More precisely, the invention relates to a process for the preparation of neopentyl glycol by hydrogenating hydroxypivaldehyde with a hydrogenation catalyst at an elevated temperature.

Neopentyl glycol and other corresponding alcohols are important intermediates, for example, in the production of various synthetic resins, such as acrylic resins polyester resins, polyurethane resins, alkyl resins and polycarbonate resins. These alcohols are also used in the preparation of plasticizers, synthetic lubricants, surfactants, etc.

Neopentyl glycol and other corresponding alcohols have conventionally been prepared by two processes. In one process, formaldehyde and aldehyde are allowed to react with a strongly alkaline catalyst, such as sodium hydroxide, potassium hydroxide or calcium hydroxide, to form alcohol, such as neopentyl glycol. However, the disadvantage of this process is that large amounts of sodium formate are formed as a by-product. The process is therefore not suitable for a commercial process unless an economically profitable use is simultaneously found for the formate.

In the other process, the aldolisation reaction of formaldehyde and aldehyde is carried out in the presence of an amine catalyst, in particular triethylamine. Neopentyl glycol is obtained, for example, by reacting formaldehyde and isobuyraldehyde in the presence of triethylamine, whereby hydroxypivaldehyde is formed as the main product. This can further be hydrogenated, whereby the desired neopentyl glycol is obtained as the end product. The aldolisation reaction can be carried out also by using an anion exchange resin as a catalyst.

Many types of catalysts have been proposed as the hydrogenation catalyst. U.S. Pat. No. 4,250,337 proposes as a catalyst copper chromite with barium as its promoter. In U.S. Pat. No. 4,855,515, the catalyst used is a mixture of copper oxide and copper chromite, with manganese oxide as promoter. In EP patent 343 475, a mixed catalyst made up of platinum, ruthenium and tungsten is used as the catalyst.

It has been observed that particularly nickel catalysts do not function satisfactorily at relatively low temperatures below 100° C. The hydroxypivaldehyde conversion and NPG conversion obtained do not reach a level adequate for commercial processes. Only with certain precious metal catalysts relatively good results have been achieved. Thus, for example, according to EP patent 343 475, a catalyst containing platinum, ruthenium and tungsten is used even at a temperature of 80° C. As solvent, water or a mixture of water and alcohol is used.

When nickel catalysts are used, the high hydrogenation temperature causes an intense increase in the amount of by-products, particularly neopentyl glycol-monoisobutyrate and hydroxypivalyl hydroxypivalate. These harmful by-products are difficult to separate from the desired neopentyl glycol, especially neopentyl glycol monoisobutyrate. Furthermore, the profitability of the manufacturing process is reduced as the selectivity decreases due to the increase in the amount of by-products. Additionally, when lower reaction temperatures are used, significantly larger amounts of the catalyst are needed, which leads to larger process volumes, and also reaction times are markedly longer, which factors render the process less suitable on an industrial scale.

The hydrogenation of hydroxypivaldehyde is usually carried out in a solvent phase. the solvent used being conventionally water. In the hydrogenation reaction, water reduces selectivity. In addition, the usable lifetime of nickel catalysts decreases significantly since a high water content tends to destroy the particle structure of the catalysts.

Thus there clearly exists a need for an improved process with superior selectivity for the preparation of neopentyl glycol with very low levels of impurities, by hydrogenation of hydroxypivaldehyde at low temperatures using commercially available nickel catalysts.

The invention relates to a process for the preparation of neopentyl glycol by hydrogenating hydroxypivaldehyde (HPA) using a nickel catalyst, in which process the amount of by-products is extremely small. Another embodiment of the invention is the manufacturing process of neopentyl glycol (NPG) where a high HPA conversion and a high NPG selectivity are obtained.

According to the invention. it has been surprisingly observed that the afore-mentioned objectives can be achieved by hydrogenating hydroxypivaldehyde at low temperatures below 100° C., and by using alcohol or ether or a mixture thereof as solvent, and by limiting the amount of water present in the hydrogenation solvent to less than 15% by weight.

In the process according to the invention, hydroxypivaldehyde used as a feed material can be prepared according to any method available. A conventional process for the preparation of hydroxypivaldehyde is to perform an aldolisation reaction where formaldehyde and aldehyde are caused to react in a so-called aldolisation reaction in the presence of an amine catalyst, in particular triethylamine. Another. even more recommendable process, is to perform a corresponding aldolisation reaction with a weak anion exchange resin acting as an aldolisation catalyst.

In the aldolisation step. formaldehyde and aldehyde are contacted with an anion exchange resin at a molar ratio of 10:1–1:10, preferably 5:1–1:5. The reaction can be carried out at a temperature of 15–100° C. When using an anion exchange resin, the upper limit for the temperature is set by the thermal resistance of the anion exchange resin used. The aldolisation reaction can be carried out as a batch process or a semi-batch process or preferably as a continuous process.

As a catalyst, weakly basic anion exchange resins are used in which the functional group is a primary amine (—$NH_2$), a secondary amine (—NHR, where R is an alkyl or an aryl) or a tertiary amine (—$NR_2$ where R is as above) or mixtures thereof. The resin matrix used can be, for example, condensation products of epichlorohydrine with amine or ammonia, phenolic resins, acrylic resins, or styrene copolymers, such as chloromethylated styrene-divinylbenzene copolymer.

The aldolisation reaction can also be carried out by using solvents. Suitable solvents include, among others, water and various alcohols, such as methanol, ethanol, n-propanol. isopropanol, n-butanol and isobutanol, or mixtures thereof, the amount of which in the reaction solution may vary within a range of 0–50% by weight. preferably within a range of 0–30% by weight.

After the aldolisation step and, if necessary, after the separation of the aldolisation catalyst, the reaction mixture is fed without any further separation measures directly to hydrogenation. According to the invention, a catalyst comprising nickel is used as the hydrogenation catalyst. The amount of nickel in the catalyst may be 60–99% by weight. The catalyst may also contain chromium and the amount of chromium may be 1–40% by weight. The catalyst may also be combined with a suitable carrier which can be an inorganic oxide, such as silica. Said catalysts are conveniently commercially available, and no special catalysts are needed.

According to the invention, the hydrogenation is carried out at a low temperature in the presence of a solvent. As solvents, alcohols or ethers or mixtures thereof are used. Suitable alcohols include, for example, methanol, ethanol, propanol, butanol, hexanol, octanol, neopentyl glycol and butyl ether or dioxane. The amount of the solvent may vary within a range of 1–70% by weight, but preferably within a range of 10–50% by weight. The purpose of the solvent is to increase the solubility of hydroxypivaldehyde in the liquid phase, since at low operating temperatures the solubility of HPA is reduced wherefore it may precipitate in the reaction solution. This can occur particularly when the conversion during the aldolisation step is hitch and thus the HPA concentration is high in the reaction mixture.

According to the invention, the hydrogenation is performed at a temperature below 100° C., preferably 60–90° C. The hydrogenation pressure may vary within a range of 1–200 bar, preferably 10–80 bar. The selectivity of the hydrogenation reaction is at least 98% due using lower operating temperatures. Additionally formation of ester impurities is practically elimited and retro-aldolisation reaction is avoided thus increasing the overall yield of the process. In the case when the aldolisation reaction is carried out using a weak anion exchange resin as an aldolisation catalyst aid-free feed is obtained and mild operation conditions in the hydrogenation step are suitable, because formation of ester impurities and acetals is avoided and there is no need for hydrogenolysis of ester impurities at high temperatures. The hydrogenation may be carried out as a batch or a semi-batch process, or preferably as a continuous process.

In the hydrogenation, it is important that the feed solution contains as little water as possible. Thus the amount of water in the solution to be hydrogenated is 15% by weight at the most, preferably lower, or the reaction mixture to be hydrogenated does not contain any water at all. Excess water may cause an increase in the quantity of by-products and a reduction in the selectivity and conversion in the formation of neopentyl glycol.

After the hydrogenation reaction, the desired alcohol, i.e., neopentyl glycol, is separated from the reaction mixture by a suitable method, for example, by distillation, and the solvents used may be recycled to the hydrogenation and/or aldolisation step.

The hydrogenation of hydroxypivaldehyde in the presence of a catalyst comprising nickel at low temperatures of 100° C. or below is especially suitable for larger. industrial scales because of the improved selectivity and good conversion. Surprisingly small amounts of the catalyst comprising nickel are needed and this results in a need for smaller reaction volumes. thus rendering the process more economical.

In the following, the invention is described in more detail with reference to the accompanying examples which are nevertheless not intended as limiting the invention.

EXAMPLE 1

Hydroxypivaldehyde (HPA) was hydrogenated in the presence of a Ni/Cr catalyst in a Parr-reactor with a volume of 300 ml. The nickel content of the catalyst was approx. 69% by weight and the chromium content approx. 13% by weight. Silica was used as the carrier agent of the catalyst. The feed solution comprised unpurified hydroxypivaldehyde in an amount of 160 g obtained by an aldolisation reaction catalysed by a weak anion exchange resin. Hydrogenation was carried out at a temperature of 70° C. and at a pressure of 70 bar using methanol as a solvent. The hydrogenation time was 240 minutes.

The properties of the feed solution and the produced reaction mixture are presented in the accompanying Table 1.

TABLE 1

| Compound | Feed (wt-%) | Product (wt-%) |
|---|---|---|
| HPA | 33.0 | 3.0 |
| NPG | 0.08 | 30.5 |
| HPHP | 0.08 | 0.17 |
| NPG-mibut | 0.04 | 0.06 |
| IBAL | 4.34 | 0.11 |
| MeOH | 50.4 | 50.0 |
| IBUOH | — | 4.21 |
| H$_2$O | 11.8 | 11.8 |
| HCOOH | — | — |
| Others | 0.26 | 0.15 |

HPA=hydroxypivaldehyde, NPG=neopentyl glycol, HPHP=hydroxypivalyl hydroxypivalate, NPG-mibut= NPG-monoisobutyrate, IBAL=isobutyraldehyde, MeOH=methanol, IBUOH=isobutanol, HCOOH= formic acid, Others=formaldehyde and unidentified compositions.

NPG selectivity was 98.5% calculated from the product analysis. HPA conversion was 91% calculated from the product analysis.

The example shows that hydrogenation can be carried out even at 70° C. with good yield when a nickel catalyst is used as a catalyst and alcohol as a solvent and when the amount of water is less than 15% by weight of the feed solution. The quantity of by-products was remarkably small.

EXAMPLE 2

Hydrogenation of HPA was performed in a continuous trickle bed reactor and experiment arrangements are described in the following:

| | |
|---|---|
| Reactor: | Tube reactor, diameter 16 mm, length 400 mm |
| Catalyst: | Ni/Cr on silica support, total Ni-content 69 wt-% (Ni, NiO), total Cr-content 13 wt-%, the catalyst was crushed to an average particle size of 1 mm |
| Feed: | Crude HPA from aldolisation without any purification operations, aldolisation catalysed by a weak anion exchange resin |
| Solvent: | methanol |
| Catalyst amount: | 6 g, silicon carbide was used as inert diluent material above and below the actual catalyst bed |
| Liquid feed rate: | 12 g/h |
| Temperature: | average bed temperature 70° C., temperature measured at 3 different points along the catalyst bed |
| Pressure: | 70 bar (abs) |
| Space velocity | WHSV = 2 |
| Operation mode: | The feed was pumped continuously through the reactor and collected in a cooled product drum, excess of hydrogen was used measured with a gas flow meter at a gas outlet stream from the product drum. The reactor temperature was controlled using electric heaters around the reactor shell. |

The properties of the feed stream and product stream compositions in steady state conditions are shown in the following table 2.

TABLE 2

| Compound | Feed (wt-%) | Product (wt-%) |
|---|---|---|
| HPA | 34.8 | 2.34 |
| NPG | 0.16 | 33.08 |
| HPHP | 0.11 | 0.19 |
| NPG-mibut | 0.03 | 0.03 |
| IBAL | 2.66 | 0.13 |
| MeOH | 49.7 | 49.9 |
| IBUOH | 0 | 2.43 |
| $H_2O$ | 11.7 | 11.7 |
| HCOOH | 0.02 | 0.02 |
| Others | 0.82 | 0.18 |

NPG selectivity was 99.7% calculated from the product analysis. Conversion of HPA was 93.2%, which can be increased by decreasing the feed rate and thus the space velocity WHSV.

What is claimed is:

1. A process for the preparation of neopentyl glycol which comprises hydrogenating hydroxypivaldehyde (HPA) in the presence of hydrogen and a hydrogenation catalyst at an elevated temperature, wherein the hydrogenation of hydroxypivaldehyde is carried out in the presence of a catalyst containing nickel or nickel-chromium and at a temperature below 100° C. and under a pressure of 10–80 bars in a liquid phase comprising solvent in an amount of 1–70% by weight and water in an amount less than 15% by weight, wherein said hydroxypivaldehyde is obtained by aldolization of formaldehyde and isobutyraldehyde with a weakly basic anion exchange resin acting as an aldolization catalyst.

2. The process according to claim 1, wherein the solvent is an aliphatic alcohol or ether or a mixture thereof.

3. The process according to claim 1, wherein the solvent is methanol, ethanol, n-propanol, isopropanol, n-butanol or isobutanol, or a mixture thereof.

4. The process according to claim 1, wherein the solvent is used in an amount of 10–50% by weight of the reaction mixture going to the hydrogenation.

5. The process according to claim 1, wherein the hydrogenation catalyst contains chromium in an amount of 1–40% by weight.

6. The process according to claim 1, wherein inorganic oxide is used as a carrier of the hydrogenation catalyst.

7. The process according to claim 1, wherein the aldolization catalyst is a weakly basic anion exchange resin, in which the functional group is a primary amine (—$NH_2$), a secondary amine (—NHR, where R is an alkyl or an aryl) or a tertiary amine (—$NR_2$ where R is as above) or mixtures thereof.

8. The process according to claim 6, wherein said inorganic oxide is silica.

* * * * *